United States Patent [19]

Coquelet et al.

[11] Patent Number: 4,665,085
[45] Date of Patent: May 12, 1987

[54] AMIDINES, PREPARATION PROCESS AND THERAPEUTICAL APPLICATION THEREOF

[75] Inventors: Claude Coquelet, Saint-Gely-Du-Fesc; Elisabeth Battais, Montpellier; Claude Bonne, Bry-sur-Marne; Daniel Sincholle, Saint-Gely-du-Fesc, all of France

[73] Assignee: Laboratoires Chauvin-Blache, Montpellier, France

[21] Appl. No.: 717,185

[22] PCT Filed: Jul. 6, 1984

[86] PCT No.: PCT/FR84/00170

§ 371 Date: Mar. 12, 1985

§ 102(e) Date: Mar. 12, 1985

[87] PCT Pub. No.: WO85/00366

PCT Pub. Date: Jan. 31, 1985

[30] Foreign Application Priority Data

Jul. 13, 1983 [FR]  France ............................ 83 11717

[51] Int. Cl.$^4$ ................ A61K 31/155; A61K 31/415; C07D 233/52; C07C 133/10
[52] U.S. Cl. .................................... 514/398; 514/632; 548/351; 564/228
[58] Field of Search ...................... 564/237, 238, 228; 548/351; 514/632, 398

[56] References Cited

U.S. PATENT DOCUMENTS 3,174,978  3/1965  Marxer ............................. 564/228
3,211,746  10/1965 Marxer ............................. 564/228

FOREIGN PATENT DOCUMENTS 0035393  9/1981  European Pat. Off. .
0043659  1/1982  European Pat. Off. .
0081924  6/1983  European Pat. Off. .
1549283  12/1968 France .
8343M    2/1971  France .
1332543  of 1982 France .
448057   12/1968 Switzerland ........................ 564/228

OTHER PUBLICATIONS

Boehringer, Ingelheim GMBH Chemical Abstracts (1968) #47,453k (S. A. 6,706,503).

Primary Examiner—Natalie Trousof
Assistant Examiner—L. Hendriksen
Attorney, Agent, or Firm—Young & Thompson

[57] ABSTRACT

Compounds having the formula (I) wherein $R_1$ and $R_2$ are a hydrogen atom, an alkyl group or a hydroxy group, or else $R_1$ and $R_2$ form together a bivalent ethylene or trimethylene radical; $R_3$ is a halogen atom, an alkyl group, an alkoxy group, a mono- or polyhydroxylated alkyl group, an amino group, a mono- or di-alkyl amino group, an acetamido or sulfonamido group; $R_1$ is a hydroxy group, a mono- or polyhydroxylated alkyl group, an amino group, a mono- or dialkyl amino group, an acetamido or sulfonamido group; $R_4$ being in the position 3, 4 or 5 and A is a bridge having from 1 to 3 links selected among the groups having the formula (II), —NH—, —N═—O— and —S—. $R_5$ represents an hydrogen atom, an alkyl group, a hydroxy group or an alkoxy group as well as the addition salts thereof with pharmaceutically acceptable acids. Said compound may be used in therapeutic treatment as antihypertensive agents, particularly in the ocular field.

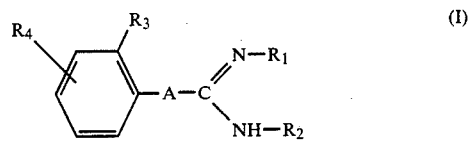

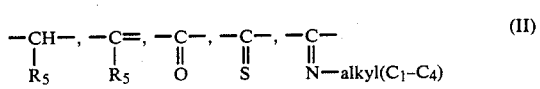

3 Claims, No Drawings

AMIDINES, PREPARATION PROCESS AND THERAPEUTICAL APPLICATION THEREOF

This invention relates to new amidines having an anti-hypertensive activity, and which are typically useful for the treatment of ocular hypertensions such as glaucoma.

The ocular hypertension phenomena are principally related to an imbalance between the rate of formation and the rate of flow of the aqueous humor.

The aqueous humor is produced by the ciliary body; it enters the posterior chamber, flows through the pupil and into the anterior chamber at the periphery of which it reaches the iraidocorneal angle. The apex of this angle is filled with a large mesh connective tissue: the trabeculum. At this level, the aqueous humor percolates the trabecular mesh, is collected in Schlemm's canal and then, via the aqueous veins, reaches the episcleral venous circulation and, finally, the systemic circulation.

In the subjects suffering from glaucoma, the rate of elimination of the aqueous humor is reduced, which results in an accumulation of aqueous humor and an ocular hypertension.

In the absence of treatment, this high pressure may interfere with the circulation of blood at the level of the nerve fibers of the retina and of the optic nerve, leading to the destruction of the optic nerve and blindness.

Examples of products commonly used in the treatment of glaucoma include:
cholinergic agents, such as pilocarpine;
carbonic anhydrase inhibitors, such as acetazolamide;
adrenergic agents, such as epinephrine, a non selective $\alpha$ and $\beta$ agonist, and timolol, a non selective $\beta$ sympathicolytic agent.

Different sudies have shown that the topical administration of products that stimulate the $\alpha_2$ adrenergic receptors, such as clonidine and $\alpha$-methyl epinephrine, produces a decrease of the intraocular pressure (ALLEN R. C., Invest. Ophthalmol., 15, (10), 815, 1976; KRIEGLSTEIN G. K., Invest. Ophthamlol. Vis. Sci. 17 (2), 149, 1978; HODAPP E., Arch. Ophthalmol., 99, 1208; 1981; LANGHAM M. E., Invest. Opthalmol. Vis. Sci. ARVO suppl., 22,230, 1982).

Due to its action on the central nervous system, clonidine exhibits detrimental side effects, in addition to its action on the intraocular pressure.

Also, in BSM 8175 and 7689 are described amidines of benzylidene amino guanidine type, for the systemic treatment of arterial hypertension. Such compounds include a sedative component, in view of their action on the central nervous system.

This invention is based on the discovery of new amidines which possess a stimulating $\alpha_2$ adrenergic activity and which are practically free from any action on the central nervous system, and which are useful as antihypertensive agents, particularly in the ocular domain.

Thus, this invention relates to compounds of the formula

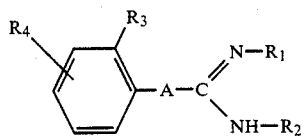

(I)

in which:

$R_1$ and $R_2$, independently from one another, represent a hydrogen atom, a $C_{1-6}$alkyl group or a hydroxy group; or $R_1$ and $R_2$ form together a divalent ethylene or trimethylene radical;

$R_3$ represents a halogen atom, a $C_{1-4}$alkyl group, a $C_{1-4}$alkoxy group, a mono- or polyhydroxy($C_{1-4}$alkyl) group, an amino group, a (mono- or di-$C_{1-4}$alkyl)amino group, an acetamido group, or a sulfonamido group;

$R_4$ represents a hydroxy group, a mono- or polyhydroxy($C_{1-4}$alkyl)group, an amino group, a (mono- or di-$C_{1-4}$alkyl)amino group, an acetamido group or a sulfonamido group, $R_4$ being at 3, 4 or 5 position; and A represents a bridge with 1-3 members selected from the groups of the formula

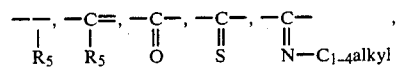

—NH—, —N=, —O— and —S—, in which $R_5$ represents a hydrogen atom, a $C_{1-4}$alkyl group, a hydroxy group, or a $C_{1-4}$alkoxy group, and their pharmaceutically acceptable acid addition salts.

This invention includes also within its scope therapeutic compositions comprising, as active ingredient, a compound of the formula (I) or a pharmaceutically acceptable acid addition salt thereof.

In the above definition, by the term "pharmaceutically acceptable acid addition salts" are meant the salts which possess the biological properties of the free bases, without having an undesirable effect. Such salts may typically by those formed with inorganic acids such as hydrochloric acid, hydrobromic acid, sulfuric acid, nitric acid, phosphoric acid, acidic metal salts such as disodium orthophosphate and monopotassium sulfate, and organic acids such as formic acid, acetic acid, propionic acid, glycolic acid, oxalic acid, fumaric acid, citric acid, malic acid, methanesulfonic acid, lactic acid, succinic acid, tartaric acid and pamoic acid.

The term "halogen" denotes chlorine, bromine or iodine.

The bridge A, which has essentially a linking function, may typically be selected from the following groups:

(a) a group of the formula

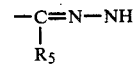

in which $R_5$ has the above defined meaning;

(b) a group of the formula —$C_nH_{2n}$— in which n has a value from 1 to 3, such as the methylene, ethylene, trimethylene and ethylidene groups;

(c) a group of the formula —O—$C_nH_{2n}$ in which n=1 or 2;

(d) the group

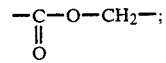

(e) a group of the formula —$C_nH_{2n}$—NH— in which n=0-2;

(f) the group —$CH_2$—NH—NH—;

(g) a group of the formula $-(C_nH_{2n-1}OH)-$ in which n=1-3, such as the hydroxy-methylene and hydroxy-ethylene groups;

(h) the thio group —S—;

(i) a group of the formula —(CH$_2$)$_n$—CH=N— in which n=0 or 1, (j) a group of the formula (CH$_2$)$_n$—NH—CH$_2$— in which n=0 or 1, (k) a group of the formula $$-(CH_2)_n-\underset{\underset{O}{\|}}{C}-NH-$$

in which n=0 or 1, (l) the group —CH$_2$—O—CH$_2$—

A preferred class of compounds of the formula (I) is formed by the compounds of the formula:

$$\text{(II)}$$

in which:

R$_1$ and R$_2$ represent each a hydrogen atom, or form together a divalent ethylene radical;

R$_3$ represents a halogen atom, a methyl group, a methoxy group, an amino group, an acetamido group or a sulfonamido group;

R$_4$ represents a hydroxy group, an amino group, an acetamido group or a sulfonamido group, and R$_5$ represents a hydrogen atom or a methyl group, and their pharmaceutically acceptable acid addition salts.

The compounds of the formula (I) may be prepared generally by reaction of a benzene compound of the formula:

$$\text{(III)}$$

with an amidine of the formula:

$$\text{(IV)}$$

in which R$_1$, R$_2$, R$_3$ and R$_4$ have the above defined meanings, and Z$_1$ and Z$_2$ are groups which, by reaction, give a group A, or by conversion of a compound of the formula:

$$\text{(V)}$$

in which R$_3$ and R$_4$ have the above defined meanings and Z$_3$ is a group convertible to a group $$-C\begin{smallmatrix}N-R_1\\ \\NH-R_2\end{smallmatrix}$$

to a compound of the formula (I).

Thus, to prepare compounds of the formula (I) in which A is a group $$-\underset{R_5}{C}=N-NH-$$

an aldehyde or a ketone of the formula:

$$\text{(VI)}$$

in which R$_3$, R$_4$ and R$_5$ have the above defined meanings, may be reacted with a compound of the formula:

$$H_2N-NH-C\begin{smallmatrix}NR_1\\ \\NHR_2\end{smallmatrix} \quad \text{(VII)}$$

in which R$_1$ and R$_2$ have the above defined meanings, or a salt thereof.

Particularly, in the case when R$_1$ and R$_2$ do no form a ring, the reaction may be conducted in n-butanol solution, in the presence of a concentrated acid such as hydrochloric acid, the water of the by-product being removed azeotropically.

A compound of the formula (VII) may also be reacted with the ketone of aldehyde of the formula (VI) by heating within pyridine.

In the case when R$_1$ and R$_2$ form a ring, the reactions well known by those skilled in the art for the synthesis of hydrazones may be used. Thus, the aldehyde or ketone of the formula (VI) may be reacted with a cyclic compound of the formula (VII) by refluxing equimolar amounts of the compounds in alcohol solution, in the presence of an acidic catalyst such as acetic acid or hydrochloric acid. A salt of a cyclic compound of the formula (VII), such as the hydrobromide or the hydrochloride, may also be reacted under the same conditions.

To prepare compounds of the formula (I) in which A is a group —C$_n$H$_{2n}$—, —O—C$_n$H$_{2n}$— or $$-\underset{\underset{O}{\|}}{C}-O-CH_2-$$

such as defined under (b), (c) and (d) above, ethanol may be reacted with a nitrile of the formula

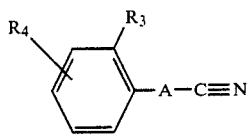

to give a compound of the formula

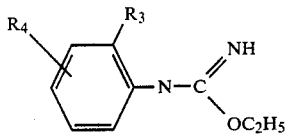

the resulting compound (IX) being then reacted with ethylenediamine, trimethylene diamine or an amine of the formula $NH_2R_2$ or a salt thereof, such as the chloride.

In addition, to prepare compounds of the formula (I) in which A is a group —$OCH_2$—, a phenol of the formula (X)

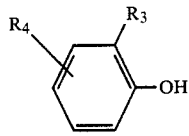

in which $R_3$ and $R_4$ have the above defined meanings, may be reacted with a chloro derivative of the formula (XI)

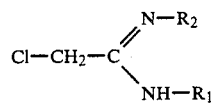

in which $R_1$ and $R_2$ have the above defined meanings.

To prepare compounds of the formula (I) in which A is a group —$C_nH_{2n}$—NH— or group —$CH_2$—NH—NH— such as defined under (e) and (f) above, a compound of the formula (XII)

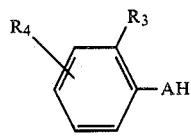

in which $R_3$ and $R_4$ have the above defined meanings, may be reacted with an S-alkyl-isothiourea of the formula (XIII)

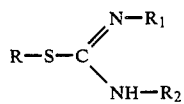

in which $R_1$ and $R_2$ are as defined above and R represents an alkyl group containing 1 or 2 carbon atoms.

To prepare compounds of the formula (I) in which A is a group —($C_nH_{2n-1}$—OH)— such as defined under (g) above, a compound of the formula (XIV)

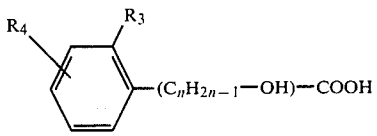

in which $R_3$ and $R_4$ have the above defined meanings, may be reacted with ethylene diamine of trimethylene diamine.

To prepare compounds of the formula (I) in which A is a —S— group, a compound of the formula (XV)

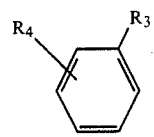

in which $R_3$ and $R_4$ have the above defined meanings, may be submitted to an oxydative coupling with a thiourea of the formula (XVI)

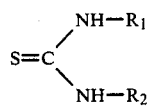

in which $R_1$ and $R_2$ have the above defined meanings.

To prepare compounds of the formula (I) in which A is a group —$(CH_2)_n$—CH=N— such as defined under (i) above, an aldehyde of the formula (XVII)

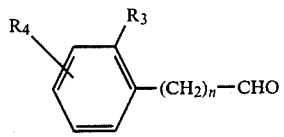

in which $R_3$ and $R_4$ have the above defined meanings and n=0 or 1, may be reacted with a compound of the formula (XVIII)

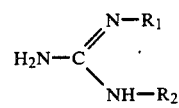

in which $R_1$ and $R_2$ have the above defined meanings.

To prepare compounds of the formula (I) in which A is a group —$(CH_2)_n$—NH—$CH_2$— such as defined under (j) above, a compound of the formula (XIX)

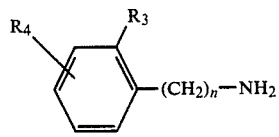

in which $R_3$ and $R_4$ have the above defined meanings, may be reacted with a chloro derivative of the formula (XI) such as defined above.

To prepare compounds of the formula (I) in which A is a group —$(CH_2)_n$—CO—NH— such as defined under (k) above, a compound of the formula (XX):

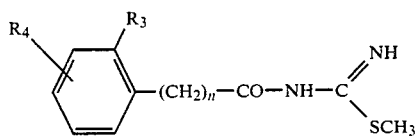
(XX)

in which $R_3$ and $R_4$ have the above-defined meanings and $n=0$ or 1, may be reacted with ethylene diamine, trimethylenediamine or an amine of the formula $HN_2R_2$.

The compound of the formula (XX) may be obtained from an acid chloride of the formula (XXI)

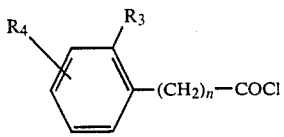
(XXI)

by reaction with ammonium isothiocyanate, followed by methylation.

To prepare compounds of the formula (I) in which A is group —$CH_2$—O—$CH_2$—, a benzyl chloride of the formula (XXII)

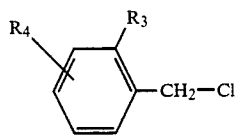
(XXII)

in which $R_3$ and $R_4$ have the above defined meanings, may be reacted with a compound of the formula (XXIII)

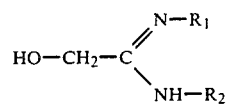
(XXIII)

in which $R_1$ and $R_2$ have the above defined meanings.

The pharmaceutically acceptable acid addition salts may be prepared in a conventional manner, by reaction of the free bases with an acid or a salt, typically in alcohol solution.

In following Table I are given Examples of compounds of this invention.

The compounds have been prepared according to the following procedures:

Procedure A

Equimolar amounts of aldehyde or ketone (VI) and of hydrazino-2-imidazoline hydrobromide are refluxed within methanol in the presence of a catalytic amount of acetic acid, for a period of time which may vary between 15 minutes and 2 hours. After cooling, the resulting hydrazone is isolated after bubbling ammonia through the methanol solution, after which the methanol is evaporated in vacuo. The crude product is converted to the hydrochloride by bubbling hydrochloric acid gas through an alcohol solution of the base. The crude salt is recrystallized from methanol-diethyl ether.

Procedure B 0.1 mole aldehyde or ketone (VI), 0.1 mole aminoguanidine bicarbonate, 10 ml concentrated hydrochloric acid and 50 ml n-butanol are refluxed in a flask provided on top with a Dean-Stark trap, for 3 hours. After removal of the solvent in vacuo, the residue is triturated in a solution of ethyl ether saturated with HCl gas. The resulting crude crystals are recrystallized from methanol-diethyl ether.

TABLE I

COMPOUNDS OF THE FORMULA (II)

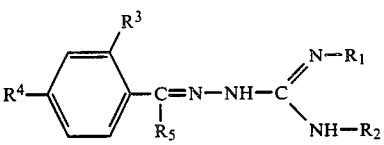

| Compound | $R_1$, $R_2$ | $R_3$ | $R_4$ | $R_5$ | Procedure | Yield (%) | Melting Point (°C.) of the Hydrochloride |
|---|---|---|---|---|---|---|---|
| 1 | —$CH_2$—$CH_2$ | $CH_3$ | OH | H | A | 64 | >255 |
| 2 | " | $CH_3$ | $NH_2$ | H | A | 70 | >255 |
| 3 | " | $CH_3$ | OH | $CH_3$ | A | 62 | 175–177 |
| 4 | " | $OCH_3$ | OH | H | A | 63 | 198 (dec.) |
| 5 | " | $OCH_3$ | $NH_2$ | H | A | 54 | 207–209 |
| 6 | " | $OCH_3$ | OH | $CH_3$ | A | 70 | 166–168 |

| Compound | $R_1$ | $R_2$ | $R_3$ | $R_4$ | $R_5$ | Procedure | Yield (%) | Melting Point (°C.) of the Hydrochloride |
|---|---|---|---|---|---|---|---|---|
| 7 | H | H | $CH_3$ | OH | H | B | 51 | 205–207 |
| 8 | H | H | $CH_3$ | $NH_2$ | H | B | 62 | 254–256 |
| 9 | H | H | $OCH_3$ | OH | H | B | 45 | 219–221 |
| 10 | H | H | $CH_3$ | OH | $CH_3$ | B | 50 | 168–170 |
| 11 | H | H | $OCH_3$ | OH | $CH_3$ | B | 55 | 193–195 |

The following non-limiting Examples are also given to illustrate this invention.

Preparation of 2-methyl-4-hydroxy-anilino-2-imidazoline hydrochloride (Compound 12)

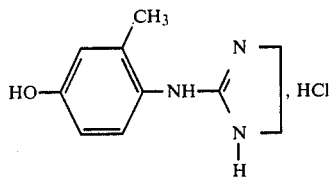

Equimolar amounts of 4-amino-m-cresol and 2-thioethyl-2-imidazoline hydrochloride are refluxed within ethanol, for 96 hours. After cooling, the ethanol solution is made basic by addition of ammonia. After removal of the solvent in vacuo, the oily residue is washed with diethyl ether and is then dissolved in acetone. The hydrochloride obtained by addition of a saturated ethereal solution of hydrochloric acid gas is recrystallized from acetone-ethyl acetate. M.p.=202°-204° C.

Preparation of 2-methyl-4-hydroxy-anilino-methyl-2-imidazoline hydrochloride (Compound 13)

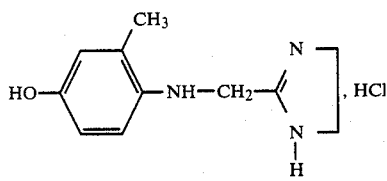

Two moles 4-amino-m-cresol and 1 mole 2-chloromethyl-2-imidazoline hydrochloride are refluxed for 3 hours, within absolute ethanol. After cooling, the insoluble fraction is suction filtered and the ethanol solution is evaporated in vacuo. The evaporation residue is recrystallized from methanol:diethyl ether; M.p.=205°-207° C.

The results of biochemical, pharmacological and toxicological investigations that demonstrate the properties of the compounds of the formula (I) are given below.

1. Affinity for platelet $\alpha_2$ adrenergic receptors

The compounds of the formula (I) were tested on the platelet adrenergic receptor of rabbit which is exclusively of $\alpha_2$ type (MICHEL T., Nature, 288, (5792) 709, 1980).

The affinity of said compounds for the $\alpha_2$ receptors is determined by measuring the inhibition of the specific linking of tritiated dihydroergocryptine (DHE) by the test compounds.

The rabbits used are male New-Zealand albino rabbits

Blood is taken by the intracardiac route, over ACD (an anticoagulant consisting of an aqueous solution containing 0.27 g citric acid, 0.5 g trisodium citrate and 0.02 g glucose per 20 ml water) at a rate of 1 volume ACD per 6 volumes blood.

The blood is centrifuged 10 minutes at 280 g and the supernatant (PRP) is collected. The PRP is centrifuged 15 minutes at 2000 g.

The platelet sediment is washed twice with buffer I (Tris 50 mM, NaCl 150 mM, EDTA 20 mM, pH 7.5) and is then re-suspended in buffer II (Tris 50 mM, EDTA 5 mM, pH 7.5).

This suspension is frozen at −40° C., and is then defrosted; the procedure is repeated twice. The suspension is then homogenized, after which it is centrifuged 10 minutes at 40,000 g, at 4° C.

The centrifugation sediment is washed with buffer II and is then re-suspended in this same buffer so that the final protein concentration is of the order of 1.5 mg/ml.

The inhibition tests are effected in a final volume of 0.2 ml of buffer II containing the tritiated DHE (7 nM) and varying concentrations of test compound.

The reaction is initiated by adding 0.2 mg proteins and is continued for 30 minutes at 25° C.

The incubation is terminated by adding 2 ml buffer II and by rapidly filtering this mixture in vacuo, through Whatman GF/C filters. The filters are rapidly washed with buffer II and the radioactivity bound to the filter is determined by liquid scintillation.

The dosage required to inhibit 50 percent of the linking of the triturated DHE ($CE_{50}$) is calculated for each of the test compounds.

The results obtained are given in the following Table.

TABLE II

| Compound | $CE_{50}$ ($10^{-6}$ M) |
|---|---|
| 1 | 3 |
| 2 | 10 |
| 3 | 5.6 |
| 4 | 3 |
| 5 | 14 |
| 6 | 2.5 |
| 7 | 6.3 |
| 8 | 32 |
| 9 | 8 |
| 10 | 11 |
| 11 | 1.3 |

2. Hypotensive activity in rabbits, after topical administration

The experiments were conducted using male New-Zealand rabbits (2 kg body weight) given "ad libitum" food and drink.

The animals are given a few days to get accustomed to the animal house, are conditioned to stabling in restraining boxes, and to the ocular pressure determinations, in order to prevent pressure deviations induced by stress and handling.

The intraocular pressure is determined with an ALCON aplanation pneumatonograph, standardized by means of an isolated cornea of rabbit, under water pressure.

The compounds are tested in isotonic aqueous solution, at pH 7.25 µl of an 0.5% solution are instilled in an eye, and the intraocular pressure is determined as a function of time.

Table below gives the maximum decrease of the intraocular pressure (Δ max) with respect to the basic value at time zero (time of instillation), the time corresponding to this maximum effect (t), and the total duration of the effect.

TABLE III

| Compound | Δmax (mm Hg) | t (mn) | Duration of the effect (mn) |
|---|---|---|---|
| 1 | −3.12 ± 2.21 | 60 | 360 |
| 2 | −4.12 ± 0.95 | 60 | 300 |
| 3 | −1.83 ± 1 | 30 | 300 |

TABLE III-continued

| Compound | Δmax (mm Hg) | t (mn) | Duration of the effect (mn) |
|---|---|---|---|
| 4 | −2.5 ± 0.57 | 60 | 400 |
| 5 | −3.9 ± 0.5 | 120 | 360 |
| 7 | −0.25 ± 1.7 | 60 | — |

Under the same experimental conditions, clonidine (2,6-dichloro-anilino-2-imidazoline) and (2,6-dichlorobenzylidene-hydrazino)-2-imidazoline (Compound of Example 1 of BSM 8175) induce a hypertension in the treated eye and a concomitant decrease of the pressure in the contralateral eye, which latter effect provides evidence of an action at the level of the central nervous system. This phenomenon is absent with the compounds of the formula (I).

3. Acute toxicity

The mice used are male Swiss mice (NMRI-Han) with an average body weight of 25 g.

The acute toxicity investigation was effected by the intraperitoneal route.

The compounds were injected in aqueous solution, at three dosage levels: 50, 100 and 200 mg/kg.

Table below gives the results obtained with compounds of the formula (I), after an observation time of 48 hours.

The results are expressed as number of dead animals vs. the total number of animals treated.

TABLE IV

| Compound | 50 mg/kg | 100 mg/kg | 200 mg/kg |
|---|---|---|---|
| 1 | — | 0/3 | 0/3 |
| 2 | — | 0/3 | 3/3 |
| 3 | — | 0/3 | 3/3 |
| 4 | — | 0/3 | 0/3 |
| 5 | — | 0/3 | ND |
| 7 | — | 0/3 | 3/3 |
| 8 | — | 0/3 | 3/3 |
| 9 | 0/3 | 3/3 | 3/3 |
| 10 | — | 0/3 | 2/3 |

ND = not determined

The therapeutic compositions of this invention may be administered to humans or to animals by the topical, oral or parenteral route.

They may be formulated as solid, semi-solid or liquid preparations. Examples of said formulations include tablets, capsules, suppositories, injectable solutions or suspensions, ointments, oily or aqueous collyria, collutories, nasal and otological solutions, and also the delayed-action forms. A preferred form is constituted by collyria and ophthalmic implants.

In such compositions, the active ingredient is generally used in admixture with one or more of the usual pharmaceutically acceptable excipients, well known by those skilled in the art.

The topically administrable compositions may typically contain from 0.1% to 5% by weight active ingredient.

The orally or parenterally administrable therapeutic compositions may typically contain from 1 to 60 wt% active ingredient.

The amount of active ingredient administered is obviously dependent on the patient, on the route of administration and on the severity of the disease. However, for oral or parenteral administration, the daily dosage regimen is about 0.1–10 mg/kg/day, thus, in the case of a 100 kg human patient, from 10 mg to 1 g/day.

We claim:

1. Compounds of the formula:

$$R_4\text{-}\underset{R_5}{\underset{|}{\text{C}}}\text{=N-NH-C}\underset{NH-R_2}{\overset{N-R_1}{\diagup}}$$

(with $R_3$ on the ring)

in which:
$R_1$ and $R_2$ represent each a hydrogen atom or form together a divalent ethylene radical,
$R_3$ represents a methyl group or a methoxy group,
$R_4$ represents a hydroxy group, and
$R_5$ represents a hydrogen atom or a methyl group, and their pharmaceutically acceptable acid addition salts.

2.

$$HO\text{-}\phi(CH_3)\text{-}CH\text{=}N\text{-}NH\text{-}C\underset{NH-CH_2}{\overset{N-CH_2}{\diagup}}$$

3. Process of the treatment of ocular hypertension, which comprises administering to a human in need thereof an effective amount of a compound as claimed in claim 1, said amount being effective to reduce ocular hypertension in a human.

* * * * *